US005710344A

United States Patent [19]

Breikss et al.

[11] Patent Number: 5,710,344
[45] Date of Patent: Jan. 20, 1998

[54] PROCESS TO PREPARE A LINEAR ALDEHYDE

[75] Inventors: Anne Irisa Breikss, Hockessin; Patrick M. Burke; James Michael Garner, both of Wilmington, all of Del.; Wilson Tam, Boothwyn, Pa.

[73] Assignees: E. I. Du Pont de Nemours and Company, Wilmington, Del.; DSM N.V., Gallen, Netherlands

[21] Appl. No.: 745,238

[22] Filed: Nov. 8, 1996

[51] Int. Cl.$^6$ .................................. C07C 45/50
[52] U.S. Cl. ........................ 568/454; 568/451
[58] Field of Search ........................ 568/451, 454

[56] References Cited

U.S. PATENT DOCUMENTS

| | | | |
|---|---|---|---|
| 3,816,452 | 6/1974 | Mrowca | 260/326.61 |
| 4,668,651 | 5/1987 | Billig et al. | 502/158 |
| 4,769,498 | 9/1988 | Billig et al. | 568/454 |
| 4,885,401 | 12/1989 | Billig et al. | 568/454 |
| 5,113,022 | 5/1992 | Abatjoglou et al. | 568/454 |
| 5,235,113 | 8/1993 | Sato et al. | 568/454 |
| 5,264,616 | 11/1993 | Roeper et al. | 560/175 |
| 5,360,938 | 11/1994 | Babin et al. | 568/449 |

FOREIGN PATENT DOCUMENTS

| | | | |
|---|---|---|---|
| WO 95/18089 | 7/1995 | WIPO | C07C 69/716 |
| WO 96/16923 | 6/1996 | WIPO | C07C 45/50 |

OTHER PUBLICATIONS

Kenneth G. Moloy and Jeffrey L. Petersen, N–Pyrrolyl Phosphines: An Unexploited Class of Phosphine Ligands and Exceptional π-Acceptor Character, *J. Am. Chem. Soc.* 1995, 117, 7696–7710, Feb. 28, 1995.

*Primary Examiner*—Gary Geist
*Assistant Examiner*—Sreeni Padmanabhan

[57] ABSTRACT

The invention relates to a process for the preparation of linear aldehydes by hydroformylation of ethylenically unsaturated organic compounds in the presence of a catalyst system comprising a Group VIII metal and a bidentate organic ligand. The bidentate organic ligand is characterized in that it has two trivalent phosphorus atoms each containing at least one P—C or one P—N bond.

29 Claims, No Drawings

PROCESS TO PREPARE A LINEAR ALDEHYDE

The invention relates to a process for the preparation of linear aldehydes by hydroformylation of ethylenically unsaturated organic compounds in the presence of a catalyst system comprising a Group VIII metal and a bidentate organic ligand. The bidentate organic ligand is characterized in that it has two trivalent phosphorus atoms each containing at least one P—C or one P—N bond.

BACKGROUND OF THE INVENTION

The synthesis of an aldehyde by hydroformylation of an olefinic compound is known in the art. A catalyst for such a process is generally a soluble complex of a Group VIII transition metal having a phosphorus containing organic ligand. It is also known that the selection of the catalyst for the hydroformylation reaction has an influence on the rate and selectivity of the product aldehyde(s), but that there is no method for predicting selectivity or reactivity from the structure of a catalytic species.

U.S. Pat. No. 5,235,113 teaches a hydroformylation process in which an organic bidentate phosphite ligand containing two phosphorus atoms linked with an organic dihydroxyl bridging group is used with rhodium as a homogeneous hydroformylation catalyst. Aldehydes were produced from ethylenically unsaturated organic compounds, for example 1-octene or dimerized butadiene, using this catalyst system.

A disadvantage of the process according to U.S. Pat. No. 5,235,113 when a catalyst system with a monodentate organophosphorus ligand was used, is that the selectivity to linear organic aldehyde compounds is generally too low, particularly for a commercially attractive process when the starting organic compound is internal ethylenically unsaturated.

With some of the disclosed multidentate phosphites of U.S. Pat. No. 5,235,113, such as tetrakis[di-(2,4-di-tert-butylphenyl)phosphito]-pentaerythritol, reasonable selectivities to linear aldehydes were achieved. However, selectivity was gained only at a loss of reaction rate. But even with this publication's "high selectivity" ligands, the activity of the hydroformylation catalyst system taught is too low for a commercially attractive process. In this system, increasing the reaction temperature is not an option to provide an increase in reaction rate since these ligands are thermally unstable at higher temperatures. In addition, selectivity decreases at higher temperature because the rate of competing olefin hydrogenation reactions increases with temperature more rapidly than does the rate of the hydroformylation reaction.

Hydroformylation processes involving organic bidentate ligands containing two trivalent phosphorus atoms, in which the two phosphorus atoms are linked with a 2,2'-dihydroxyl-1,1'-binaphthalene bridging group, have been described in U.S. Pat. Nos. 4,769,498; 4,668,651; 5,113,022; 5,059,710; 5,264,616; 4,885,401; WO-A-9303839 and WO-A-9518089.

U.S. Pat. No. 4,885,401 teaches a compound with methyl substituents on both the 3 and 3' positions of this bridging group. However, there is no suggestion that the use of this class of ligands would give favorable results in producing linear aldehydes when starting from internally unsaturated organic compounds.

The preparation of organophosphorus compounds containing N-bonded pyrrole groups are described in U.S. Pat. No. 3,816,452 and in J. Amer. Chem. Soc. 1995, 117, 7707. However, there has been no teachings of the use of these compounds as ligands for olefin hydroformylation.

WO 96/16923 teaches aldehyde preparation by hydroformylation from a multidentate phosphorus amide ligands bridged by various groups.

SUMMARY OF THE INVENTION

This invention provides a process for the preparation of a linear aldehyde, comprising reacting an ethylenically unsaturated organic compound with carbon monoxide and hydrogen in the presence of a catalyst system comprising a Group VIII metal and a ligand of Formula 1.

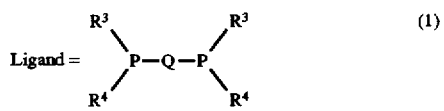

wherein Q is a 2,2'-dihydroxyl-1,1'-binaphthalene or 2,2'-dihydroxyl-1,1'-biphenylene bridging group and $R^3$ and $R^4$ are aryl or nitrogen containing heterocyclic groups, for example, pyrrole, indole or imidazole groups bonded to phosphorus through the nitrogen atom.

Q shown structurally is:

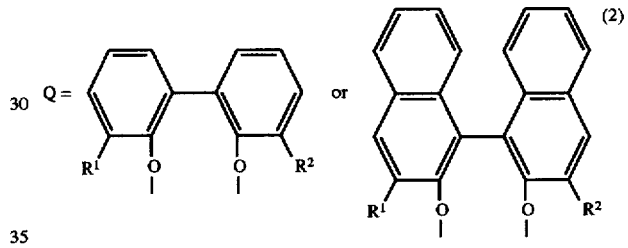

DETAILED DESCRIPTION OF THE INVENTION

Ligands of the present invention contain two trivalent phosphorus atoms in which each trivalent phosphorus atom is bonded to three organic groups. These ligands may be characterized as phosphinites or phosphorus amide compounds.

Phosphinite compounds are characterized in that the trivalent phosphorus atom is linked to the organic group with one P—O bond and two P—C bonds.

Phosphorus amide compounds are characterized in that the trivalent phosphorus atom is linked to the organic group with at least one P—N bond and one or two P—O bonds (These compounds are also known as phosphorodiamidites and phosphoramidites, respectively).

In addition, the ligands of the present invention are bidentate ligands meaning that the two trivalent phosphorus atoms in the molecule are each bonded to the same organic group bridging the trivalent phosphorus atoms together.

The aim of this invention is to provide a process for the preparation of linear aldehydes with high catalyst performance (selectivity and/or activity). The process of the present invention achieves a combination of high selectivity towards linear aldehydes and relatively high catalyst activity.

The advantages of this novel process are even more pronounced when starting from internally unsaturated organic compounds. Preparing linear aldehydes from internally unsaturated compounds using previously known hydroformylation processes generally resulted in lower selectivity to linear aldehydes, increased hydrogenation of the olefinic double bond and/or lower catalytic activity.

An additional advantage of the present process is that the linear selectivity is high. Linear selectivity, "linearity", is defined as the mole ratio of the linear aldehydes compared to the total aldehyde product from the hydroformylation reaction as shown in the equation below:

linearity=100×(linear aldehydes/(linear+branched aldehydes));

linear and branched aldehydes are illustrated in the following chemical reaction:

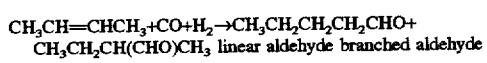

The combination of selectivity and reactivity of the present invention is achieved by using a ligand of the following formula in a Group VIII metal-catalyzed hydroformylation process:

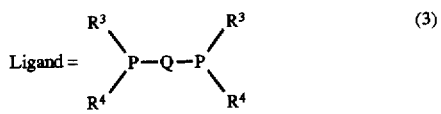

wherein, Q is a 2,2'-dihydroxyl-1,1'-binapthalene or 2,2'-dihydroxyl-1,1'-biphenylene bridging group. Q is shown structurally as:

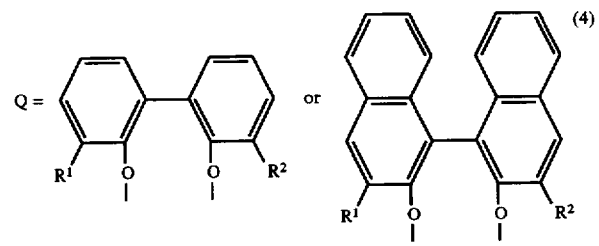

$R^1$ and $R^2$ are independently chosen from the group of hydrogen, alkyl, aryl, triarylsilyl, trialkylsilyl, carboalkoxy, carboaryloxy, aryloxy, alkoxy, alkylcarbonyl, arylcarbonyl, amide, or nitrile. Preferred amide groups are C(O)N(R5)(R7) where R5, R7 are independently C1 to C10 alkyl groups.

$R^1$ and $R^2$ are preferably a C2–C10 alkyl group, for example ethyl, propyl, isopropyl, butyl, tert-butyl, isobutyl, pentyl, or hexyl. An example of a suitable triarylsilyl group is triphenylsilyl, and examples of suitable trialkylsilyl groups are trimethylsilyl and triethylsilyl. Preferred aryl groups have 6 to 20 carbon atoms, for example phenyl, benzyl, tolyl, naphthyl, anthranyl or phenanthryl. Preferred aryloxy groups have 6 to 12 carbon atoms, for example phenoxy. Preferred alkoxy groups have 1 to 10 carbon atoms, for example methoxy, ethoxy, isopropoxy or tert-butoxy. Preferred alkylcarbonyl groups have 2 to 12 carbon atoms, for example methylcarbonyl, tert-butylcarbonyl. Preferred arylcarbonyl groups have 7 to 13 carbon atoms, for example phenylcarbonyl.

Most preferably, $R^1$ and $R^2$ are carboalkoxy or carboaryloxy groups, —CO$_2$R, in which R is $C_1$–$C_{20}$ alkyl or $C_6$–$C_{12}$ aryl. Examples of suitable R groups are methyl, ethyl, propyl, isopropyl, n-butyl, tert-butyl, isobutyl, phenyl, tolyl or naphthyl.

The 2,2'-dihydroxyl-1,1'-binaphthalene and 2,2'-dihydroxyl-1,1'-biphenylene bridging groups shown in structure 4 can optionally be further substituted with other group on the naphthalene rings.

$R^3$ and $R^4$ may be the same or different monovalent aryl groups, preferably groups with 6 to 25 carbon atoms. Preferably $R^3$ and $R^4$ are monovalent aryl groups, for example phenyl, containing at least one group, $R^6$, other than hydrogen in a meta- or para-position relative to the phosphorus atom, where $R^6$ is a electron-withdrawing group as defined by J. March, Advanced Organic Chemistry, second edition, p. 21, McGraw-Hill Book Co. Examples of $R^6$ are Cl, F, Br, CF$_3$. Other preferred groups for $R^3$ and $R^4$ are monovalent fused aromatic ring systems with 2 or more rings.

When the aryl groups $R^3$ and $R^4$ are substituted with at least one $R^6$ group in the meta- or para-position relative to the phosphorus atom, higher catalyst activity and selectivity is observed using these ligands in hydroformylation.

Another preferred class of aryl groups for $R^3$ and $R^4$ are fused aromatic ring systems with 2 or more rings, for example, 1-naphthyl or 7-phenanthryl.

$R^3$ and $R^4$ may also be the same or different nitrogen containing heterocyclic groups, for example pyrrolyl, indolyl, or imidazolyl groups where the attachment to phosphorus is through a nitrogen atom.

Examples of ligands in the present invention are:

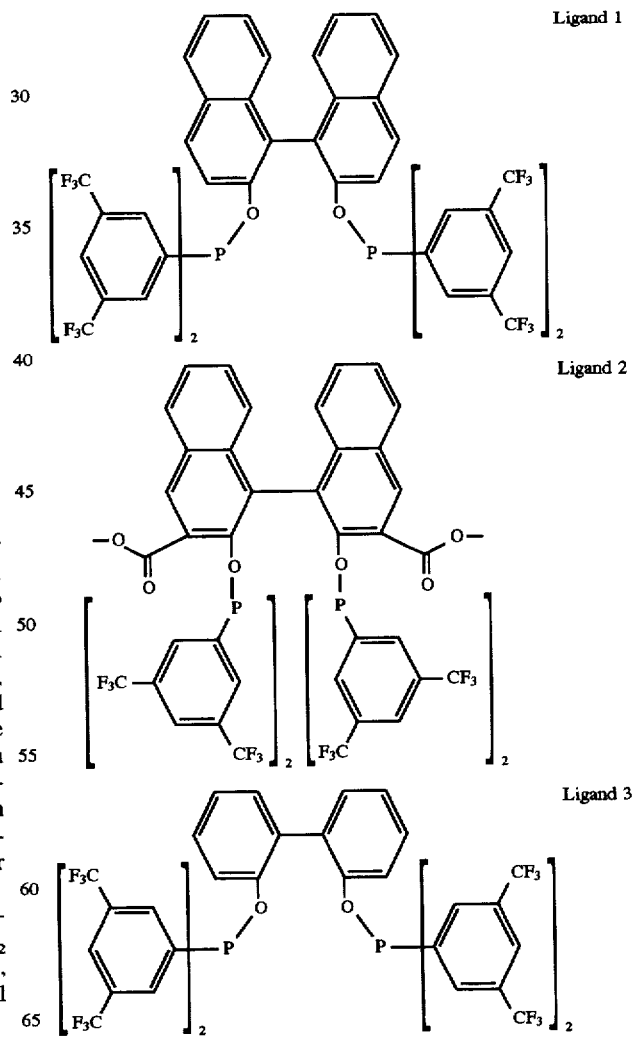

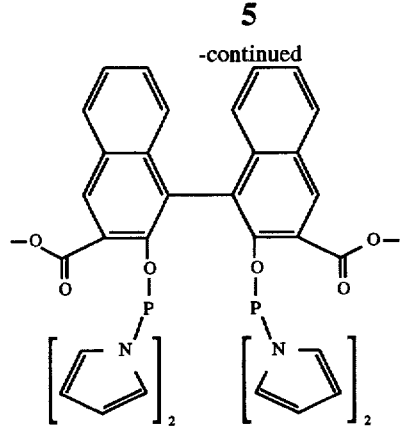

Ligand 4

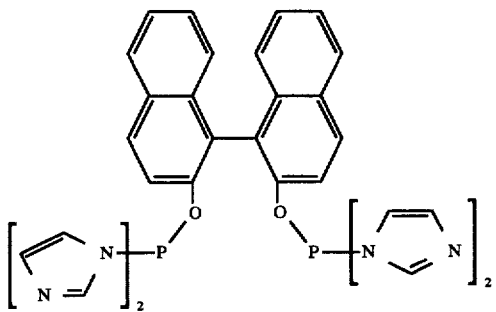

Ligand 5

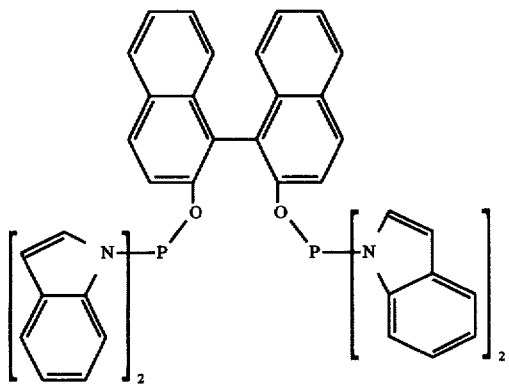

Ligand 6

The bidentate phosphinite compounds (Formula 1–3 with $R^3$ and $R^4$ being aryl) may be prepared by a variety of methods known in the art. The symmetrical diphosphinites can be prepared as follows. The diarylchlorophosphine is added to a toluene solution of a diol and triethylamine. The reaction mixture is allowed to stir at room temperature, then filtered to remove triethylamine hydrochloride. The product is isolated by removing the solvent under reduced pressure and can be purified by crystallization or chromatography.

Unsymmetrical diphosphinites may be prepared in a similar manner. The first diarylchlorophosphine (preferably the more sterically hindered one) is added to a toluene solution of a diol and triethylamine. Once the reaction is complete, the second diarylchlorophosphine is added. Triethylamine hydrochloride is filtered off and the solvent removed under reduced pressure to give the product.

The bidentate phosphorus compounds containing P—N bonded pyrrole groups may be prepared at low temperature by reacting phosphorus trichloride with two equivalents of pyrrole in the presence of triethylamine which yields ClP$(R^3)_2$ (where $R^3$ is N-bonded pyrrole to phosphorus). This intermediate phosphorus chloride compound is further reacted with a diol and triethylamine to give the desired bidentate compound. The indolyl and imidazolyl ligands were prepared in an analogous manner.

The catalyst system used in the process according to this invention can be prepared by mixing a suitable Group VIII metal compound with the phosphorus ligand, optionally in a suitable solvent, in accordance with well-known complex-forming methods. The solvent will generally be the solvent used in the hydroformylation. Suitable Group VIII metal compounds are hydrides, halides, organic acid salts, acetylacetonates, inorganic acid salts, oxides, carbonyl compounds and amine compounds of these metals. Examples of suitable Group VIII metals are ruthenium, rhodium, and iridium. Examples of suitable Group VIII metal compounds are, for example, $Ru_3(CO)_{12}$, $Ru(NO_3)_3$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "Ac" is an acetyl group; "COD" is 1,5-cyclooctadiene; and "Ph" is a phenyl group). However, it should be noted that the Group VIII metal compounds are not necessarily limited to the above listed compounds.

The Group VIII metal is preferably rhodium.

The ethylenically unsaturated organic compound has at least one "C=C" bond in the molecule and preferably 2 to 20 carbon atoms. Examples of suitable ethylenically unsaturated organic compounds are linear terminal olefinic hydrocarbons, for example, ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons, for example, isobutene and 2-methyl-1-butene; linear internal olefinic hydrocarbons, for example, cis- and trans-2-butene, cis- and trans-2-hexene, cis- and trans-3-hexene, cis- and trans-2-octene and cis- and trans-3-octene; branched internal olefinic hydrocarbons, for example, 2,3-dimethyl-2-butene, 2-methyl-2-butene and 2-methyl-2-pentene; terminal olefinic hydrocarbon-internal olefinic hydrocarbon mixtures; for example, octenes prepared by dimerization of butenes; olefin oligomer isomer mixture from butadiene, dimer to tetramer of lower butadiene olefins including propylene, n-butene, isobutene or the like; and cycloaliphatic olefinic hydrocarbons for example, cyclopentene, cyclohexene, 1-methylcyclohexene, cyclooctene, and limonene. The invention is especially directed to hydroformylation processes in which a linear aldehyde compound is prepared starting from internally unsaturated organic compounds with 6 to 20 carbon atoms such as alkyl pentenoates.

Examples of suitable olefinic compounds include those substituted with an unsaturated hydrocarbon group including olefinic compounds containing an aromatic substituent such as styrene, α-methylstyrene and allylbenzene; and diene compounds such as 1,3-butadiene, 1,5-hexadiene, 1,7-octadiene and norbornadiene. It has been found that with the process according to this invention it is possible to prepare 3-pentenal in high yield starting from 1,3-butadiene.

The ethylenically unsaturated organic compound can be substituted with one or more functional groups containing a heteroatom, such as oxygen, sulfur, nitrogen, or phosphorus. Examples of these heteroatom-substituted ethylenically unsaturated organic compounds include vinyl methyl ether, methyl oleate, oleyl alcohol, methyl 2-pentenoate, methyl 3-pentenoate, methyl 4-pentenoate, 3-pentenoic acid, 4-pentenoic acid, 3-pentenenitrile, 4-pentenenitrile, 1,7-octadiene, 7-octen-1-al, acrylonitrile, acrylic acid esters, methyl acrylate, methacrylic acid esters, methyl methacrylate, acrolein and other substituted ethylenically unsaturated compounds.

A special class of internally unsaturated organic compounds is 3-pentenenitrile, 3-pentenoic acid and $C_1$–$C_6$ alkyl 3-pentenoate ester compounds. The linear aldehyde compound prepared by this process starting from these compounds can advantageously be used in the preparation of ε-caprolactam or adipic acid, which are precursors for Nylon-6 and Nylon-6,6, respectively. Examples of $C_1$–$C_6$ alkyl 3-pentenoates are methyl, ethyl, propyl, isopropyl, tert-butyl-, pentyl, and cyclohexyl 3-pentenoate. Methyl and ethyl 3-pentenoate esters are preferred because they are more readily available.

The 3-pentenenitrile, 3-pentenoic acid and $C_1$–$C_6$ alkyl 3-pentenoate ester compounds may be present in mixtures containing respectively: 2- and 4-pentenenitrile; 2- and 4-pentenoic acid; and $C_1$–$C_6$ alkyl 2- and 4-pentenoate ester compounds. Because these compounds react in a similar fashion as their corresponding 3-isomers to the desired linear aldehyde, the mixture of isomers can be directly used in the process according to the invention.

The hydroformylation process according to the invention can be performed as described below.

The reaction conditions of the hydroformylation process according to this invention are in general the same as used in a conventional process, described for example in U.S. Pat. No. 4,769,498, and will be dependent on the particular starting ethylenically unsaturated organic compound. For example, the temperature can be from ambient temperature to 200° C., preferably from about 50° to 150° C., and more preferably from 90° to 110° C. The pressure may vary from normal pressure to 20 MPa, preferably from 0.15 to 10 MPa and more preferably from 0.2 to 5 MPa. The pressure is, as a rule, equal to the combined hydrogen and carbon monoxide partial pressure. However, extra inert gases may also be present. The molar ratio of hydrogen: carbon monoxide is generally between 10:1 and 1:10 and preferably between 6:1 and 1:2.

The amount of Group VIII metal (compound) is not specially limited, but is optionally selected so that favorable results can be obtained with respect to catalyst activity and process economy. In general, the concentration of Group VIII metal in the reaction medium is between 10 and 10,000 ppm and more preferably between 100–1000 ppm, calculated as free metal.

The molar ratio of multidentate phosphorus ligand to Group VIII metal is not specially limited, but is optionally selected so that favorable results can be obtained with respect to catalyst activity and desired aldehyde selectivity. This ratio generally is from about 0.5 to 100 and preferably from 1 to 10 (moles ligand/mole metal).

The choice of an optional solvent is not critical. The solvent may be the mixture of reactants of the hydroformylation itself, such as the starting unsaturated compound, the aldehyde product and/or by-products. Other suitable solvents include saturated hydrocarbons (for example, kerosene, mineral oil, or cyclohexane), ethers (for example, diphenyl ether or tetrahydrofuran), ketones (for example, acetone, cyclohexanone), nitriles (for example, acetonitrile, adiponitrile or benzonitrile), aromatics (for example, toluene, benzene, or xylene), esters (for example, methyl valerate, caprolactone), texanol® (Union Carbide), or dimethylformamide.

The invention shall be illustrated with the following non-limiting examples.

EXAMPLE 1

This example illustrates the hydroformylation of methyl 3-pentenoate with Ligand 2:

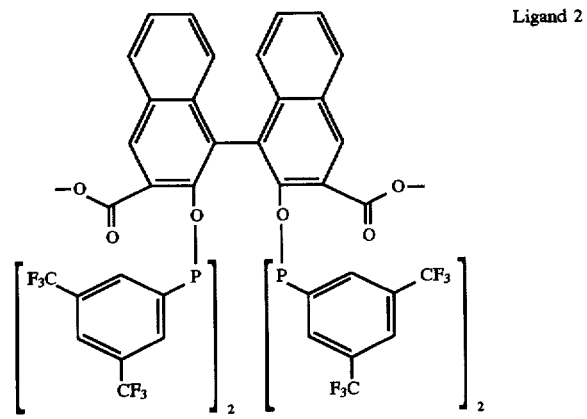

Ligand 2

First di[3,5-bis(trifluoromethyl)phenyl]chlorophosphine was prepared as follows.

The Grignard reagent of 3,5-bis(trifluoromethyl) bromobenzene in diethyl ether (0.78 moles in ca. 700 mL) was prepared with a literature procedure (Tetrahedron Lett. 1983, 24, 4703–6). With mechanical stirring under nitrogen, this solution was added dropwise to $Et_2NPCl_2$ (64.8 gm, 54 mL, 0.37 mol) and dry pyridine (123 gm, 126 mL, 1.56 mol) dissolved in dry diethyl ether (600 mL) while maintaining the reaction solution temperature below 10° C. with external cooling. After all the Grignard reagent had been added, the mixture was stirred overnight. While excluding moisture, the magnesium salts were filtered and washed with 500 mL of dry diethyl ether.

The ether filtrate was mechanically stirred in a 2 liter flask and cooled to 0° C. Hydrogen chloride gas was then bubbled through this solution until the $^{31}P$ NMR indicated the reaction was complete [$^{31}P$ NMR data for $Ar_2PNEt_2$: 57 ppm; $Ar_2PCl$: 71 ppm, where Ar=3,5-bis(trifluoromethyl) phenyl]. After all of the starting material had been converted to $Ar_2PCl$, the ether solution was evaporated and the viscous residue was taken into a drybox. Dry petroleum ether (200 mL) was added to the residue and the mixture was stirred vigorously for 1 hour. The diethylammonium and pyridinium chloride salts were filtered and washed with petroleum ether (2×100 mL). Evaporation of the filtrate followed by vacuum distillation at 0.05 mm Hg gave di[3,5-bis (trifluoromethyl)phenyl]chlorophosphine as a slightly viscous liquid boiling at 85°–95° C. The isolated yield based on $Et_2NPCl_2$ was approximately 60–70%.

Next:

Dimethyl 2,2'-dihydroxy-1,1'-binaphthalene-3,3'-dicarboxylate (6.03 gm, 15 mmol) and triethylamine (4.55 gm, 45 mmol) were dissolved in dry dichloromethane/ diethyl ether (200 mL/100 mL). Di[3,5-bis(trifluoromethyl) -phenyl]chlorophosphine (14.77 gm, 30 mmol) was added and the solution was stirred overnight at ambient temperature (12 hours). $^{31}P$ NMR was used to monitor the reaction progress. The triethylammonium chloride salts were removed by filtration then the solvent was evaporated under vacuum. The residue was dissolved in dichloromethane and passed down a short alumina plug (60 mL funnel, 4 cm diameter) eluting with the same solvent. The solvent was evaporated to yield a light yellow solid (18 gm, 91%) of the desired ligand. A yellow impurity can be removed by crystallization from diethyl ether. $^{31}P$ NMR ($CDCl_3$): 104 ppm.

The hydroformylation was accomplished as follows.

A 25 mL glass lined pressure vessel was charged with 5 mL of a solution containing 11.4 gm (100 mmol) methyl 3-pentenoate (M3P), 0.068 gm (0.2 mmol) of dicarbonyl(2,2,6,6-tetramethyl-3,5-heptanedionato) rhodium (Rh(CO)2DPM), 1.34 gm (1.0 mmol) of Ligand 2 and 1.00 gm of tetradecane (internal GC standard) in 100 mL toluene. The molar ratio of ligand to rhodium was 5. The pressure vessel was freed from air by purging first with nitrogen (twice) and then with 1:1 CO/$H_2$ (twice). The vessel was then pressurized to 75 psi CO and heated to 100° C. with agitation for 2 hours. The heat was shut off and the pressure vessel was allowed to cool to room temperature. The excess gases were vented and the products were analyzed by GC. Methyl 3-pentenoate conversion [% methyl 3-pentenoate and methyl 4-pentenoate (M4P) reacted]: 40.0%; linearity [100× methyl 5-formylvalerate (M5FV)/(methyl 5-formylvalerate+branched formylvalerates)]: 97%, Selectivity (100×M5FV/All products): 64%.

EXAMPLE 2

This example illustrates the hydroformylation of methyl 3-pentenoate with Ligand 4:

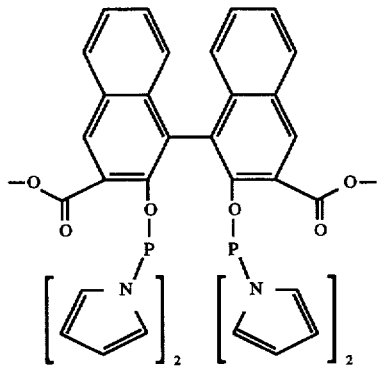

Ligand 4

First Ligand 4 was prepared as follows.

Freshly distilled phosphorus trichloride (13.7 gm, 100 mmol) and pyrrole (13.4 gm, 200 mmol) were added to dry tetrahydrofuran (500 mL) at −78° C. Anhydrous triethylamine (30.3 gm, 300 mmol) was added dropwise then the mixture was slowly warmed to ambient temperature and stirred for another 12 hours under nitrogen. Dimethyl 2,2'-dihydroxy-1,1'-binaphthalene-3,3'-dicarboxylate (14.07 gm, 35 mmol; prepared according to the literature: *J. Am. Chem. Soc.* 1954, 76, 296; *Tetrahedron Lett.* 1990, 413) was added to the tetrahydrofuran solution and the mixture was again stirred overnight. The insoluble ammonium salts were removed by filtration and the filtrate was evaporated. The residue was dissolved in the minimum amount of dichloromethane and the product was crystallized by adding diethyl ether followed by cooling to −30° C. The off-white solid was washed with cold ether and dried under vacuum. $^{31}$P NMR (CDCl$_3$) 107 ppm; $^1$H NMR (CDCl$_3$, 300 MHz, δ): 3.53 (s, 3H), 5.6 (m, 2H), 6.05 (m, 2H), 6.6 (m,2H), 6.8 (d, 1H), 7.23 (t,1H), 7.33 (t,1H), 7.75 (d, 1H), 8.33 (s,1H).

The hydroformylation was carried out as in Example 1, except that 0.72 gm (1.0 mmol) of Ligand 4 was used instead of the noted amount of Ligand 2. GC analysis indicated 77.6% methyl 3-pentenoate conversion with a M5FV selectivity of 73.0% and a linearity of 97.1%.

EXAMPLE 3

This example illustrates the hydroformylation of methyl 3-pentenoate with Ligand 1.

First Ligand I was prepared as follows.

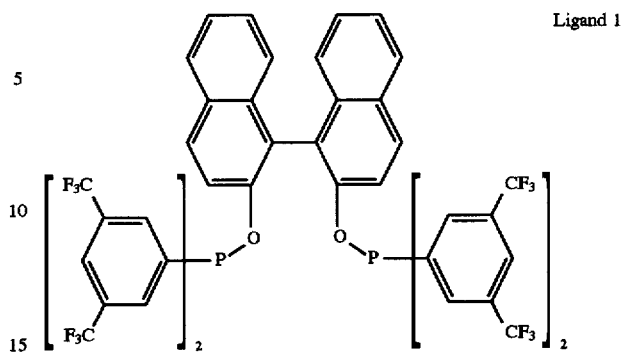

Ligand 1

Under a nitrogen atmosphere, 0.93 gm (1.89 mmol) of di[3,5-bis(trifluoromethyl)phenyl]chlorophosphine was added to a solution containing 0.27 gm (0.94 mmol) of 1,1'-bi-2-naphthol and 0.50 mL (3.59 mmol) of triethylamine in 15 mL toluene. The mixture was allowed to stir at room temperature for an hour then filtered to remove triethylamine hydrochloride. The filtrate and toluene washings of the Et$_3$N.HCl were combined and the solvent removed under reduced pressure to give 0.832 g of product. $^{31}$P NMR (CDCl$_3$): 104.4 ppm, singlet.

The hydroformylation was similar to that of Example 1 except that 1.2 gm (1.0 mmol) of Ligand 1 was used in place of the noted amount of Ligand 2. GC analysis indicated 94% methyl 3-pentenoate conversion with a M5FV selectivity of 54% and linearity of 87.7%.

EXAMPLE 4

This example illustrates the hydroformylation of methyl 3-pentenoate with Ligand 3.

Ligand 3 was prepared as follows:

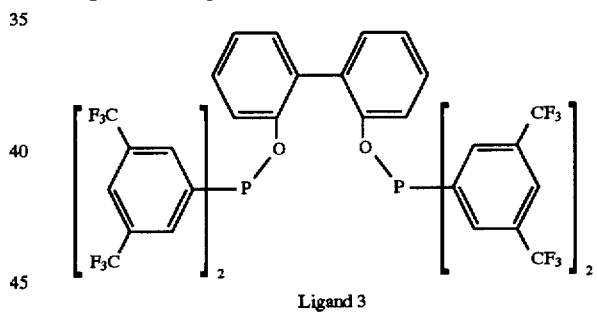

Ligand 3

Under a nitrogen atmosphere, 0.824 gm (1.67 mmol) of di[3,5-bis(trifluoromethyl)phenyl]chlorophosphine was added to a solution containing 0.157 gm (0.84 mmol) of 2,2'-biphenol and 0.65 mL (4.67 mmol) of triethylamine in 20 mL toluene. The mixture was allowed to stir at room temperature for an hour, then filtered to remove triethylamine hydrochloride. The filtrate and toluene washings of the Et$_3$N.HCl were combined and the solvent removed under reduced pressure to give 0.743 gm of product. $^{31}$P NMR (CDCl$_3$): 104.8 ppm, singlet; small amounts of impurities were present upfield of this signal.

The hydroformylation was carried out as described in Example 1 except that ligand 2 was replaced with an equivalent amount of ligand 3. GC analysis indicated 80% methyl 3-pentenoate conversion with a M5FV selectivity of 45% and linearity of 77%.

EXAMPLE 5

This example illustrates the hydroformylation of methyl 3-pentenoate with Ligand 2 in a dimethyl adipate solvent at 105° C. and 150 psi.

A 100 mL mechanically stirred Hastelloy-C autoclave was flushed with nitrogen and then with 50 psi of 1:1 $CO/H_2$. It was then charged with a solution of 22.8 gm (200 mmole) of methyl 3-pentenoate, 0.53 gm (0.4 mmole) Ligand 2, 0.5 g ortho-dichlorobenzene (ODCB, GC standard), and 16.1 gm of dimethyl adipate solvent. The autoclave was pressured with 1:1 $CO/H_2$ to 90 psi and heated to 105° C. The reaction was initiated by adding a solution of $Rh(CO)_2DPM$ (0.068 gm; 0.2 mmole) dissolved in 10 gm of dimethyl adipate. The pressure was immediately adjusted with the $CO/H_2$ feed gas to 150 psi at 105° C. 1/1 $CO/H_2$ was continuously fed to the autoclave from a reservoir so as to maintain the total pressure constant at 150 psi. Samples were removed at intervals for GC analysis. The reaction was allowed to run for a total of 21 hours after which it was cooled to 20° C. The excess $CO/H_2$ was vented through a control valve and the product was discharged.

The samples from the reactor were analyzed on a 30 M Carbowax capillary GC column and the results are shown in Table 1.

TABLE 1

| Sample Time (Minutes) | methyl 3-pentenoate Conversion (%) | M5FV Selectivity (%) | Aldehyde Linearity (%) |
|---|---|---|---|
| 5 | 13.9 | 51.2 | 96.7 |
| 20 | 38.3 | 65.3 | 96.7 |
| 30 | 48.7 | 65.4 | 96.5 |
| 60 | 69.5 | 69.5 | 96.3 |
| 120 | 86.7 | 73.6 | 96.2 |
| 185 | 93.1 | 75.3 | 96.1 |
| 360 | 98.6 | 79.7 | 95.9 |
| 1260 | 99.4 | 80.0 | 95.5 |

The initial first order rate constant was 1.25/Hr and the turnover frequency from this rate is 904 moles/mole Rh/Hr.

EXAMPLES 6–8

These examples illustrate the hydroformylation of methyl 3-pentenoate with diphosphinite ligands containing the unsubstituted 2,2'-dihydroxyl-1-1'-binaphthalene bridge and various electronegative substituents on aryl terminal groups for which the general structure is shown below for Ligands 7 to 9.

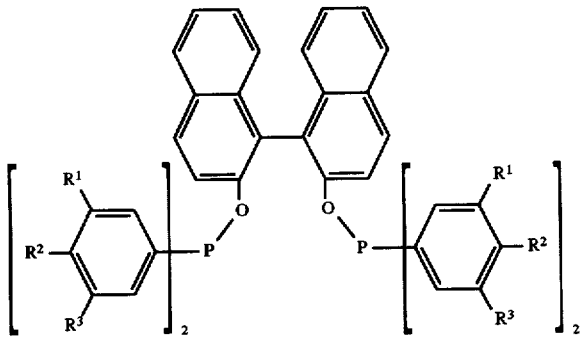

General Structure for Ligands 7–9

Ligand 7: $R^1=R^3=F$, $R^2=H$
Ligand 8: $R^1=R^2=H$, $R^3=CF_3$
Ligand 9: $R^1=R^3=H$, $R^2=Cl$ The hydroformylation was carried out as described in Example 1 except that the Ligand 2 was replaced with an equivalent amount of the Ligands 7, 8, or 9. The results are summarized in Table 2.

TABLE 2

| Example | Ligand | Conversion (%) | M5FV Selectivity (%) | Aldehyde Linearity (%) |
|---|---|---|---|---|
| 6 | 7 | 5.5 | 37 | 84 |
| 7 | 8 | 20 | 55 | 83 |
| 8 | 9 | 6.4 | 50 | 80 |

EXAMPLES 9–12

These Examples illustrate the hydroformylation of methyl 3-pentenoate with diphosphinite ligands containing 3,3'-disubstituted-2,2'-dihydroxyl-1-1'-binaphthalene bridge and 3,5-bis(trifluoromethyl)phenyl terminal groups for which the general structure is shown below the figure for Ligands 10 to 12.

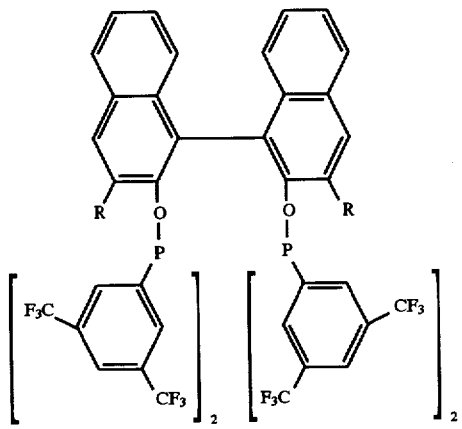

General Structure for Ligands 10–12

Ligand 10: $R=CO_2C(CH_3)_3$
Ligand 11: $R=CO_2Et$
Ligand 12: $R=C_2H_5$

TABLE 3

| Example | Ligand | Conversion (%) | M5FV Selectivity (%) | Aldehyde Linearity (%) |
|---|---|---|---|---|
| 9 | 10 | 40.9 | 68.1 | 95.1 |
| 10 | 11 | 40.0 | 64.0 | 97.0 |
| 11 | 12 | 94.0 | 55.0 | 86.0 |

EXAMPLES 12–15

These examples illustrate the hydroformylation of 1-hexene and 2-hexene with Ligands 1 and 4.

The hydroformylation was carried out as described in Example 1 except that methyl 3-pentenoate was replaced by an equivalent amount of 1-hexene or 2-hexene, the $CO/H_2$ pressure was 100 psi at the reaction temperature of 100° C., and the total reaction time was 4 hours. Ligand 1 and comparative Ligand 4 were used. Analysis of the products gave the results shown in Table 4.

13

TABLE 4

| Example | Ligand | Substrate | 1-Heptanal Selectivity (%) | Aldehyde Linearity (%) |
|---|---|---|---|---|
| 12 | 1 | 1-Hexene | 80.9 | 95.7 |
| 13 | 4 | 1-Hexene | 85.8 | 93.5 |
| 14 | 1 | 2-Hexene | 73.0 | 89.4 |
| 15 | 4 | 2-Hexene | 87.6 | 82.9 |

EXAMPLES 16 TO 20

These examples illustrate the hydroformylation of 3-pentenenitrile hydroformylation with Ligands 1, 2, and 4.

The hydroformylation was carried out as described in Example 1 except that methyl 3-pentenoate was replaced by an equivalent amount of 3-pentenenitrile (3PN) and the ligand, temperature, and pressure were varied. Analysis of the products showed a mixture of 3-, 4-, and 5-formylvaleronitriles (FVN) (aldehyde products from pentenenitrile hydroformylation) and valeronitrile (VN; reduction product). The results are summarized in Table 5.

TABLE 5

| Example | Ligand | Temp. (°C.) | Press. (psi) | React. Time (Hrs.) | 3PN Conv. (%) | 5FVN Select. (%) | Aldehyde Linearity (%) |
|---|---|---|---|---|---|---|---|
| 16 | 2 | 110 | 150 | 2 | 33.0 | 54.5 | 81.8 |
| 17 | 1 | 110 | 150 | 2 | 45.9 | 29.7 | 36.1 |
| 18 | 4 | 110 | 150 | 6 | 99.1 | 59.6 | 84.2 |
| 19 | 4 | 110 | 150 | 6 | 98.4 | 62.3 | 78.8 |
| 20 | 4 | 100 | 75 | 2 | 81.5 | 68.6 | 87.5 |

The CO/H$_2$ ratio was 65/35 in this example; the ratio was 50/50 in all other examples; *247-2B.

These results show that moderately high selectivity to the linear 5-formylvaleronitrile (5FVN; a caprolactam precursor) can be obtained with the catalysts of this invention.

EXAMPLES 21-23

These examples illustrate the hydroformylation of 1,3-butadiene with Ligands 1, 2, and 4.

The hydroformylation was carried out as described in Example 1 except that methyl 3-pentenoate was replaced by an equivalent amount of 1,3-butadiene and that the solvent was tetrahydrofuran, the pressure was 1000 psi (6.8 Mpa), the temperature was 90° and Ligands 1, 2 or 4 (moles ligand/mole Rh=3 or 6) were used. Analysis of the products showed a mixture of pentenals (primarily trans 3-pentenal), pentanal (reduction product), and C$_6$ dialdehydes (primarily 1,4-butanedial). The results are summarized in Table 6.

TABLE 6

| Example | Ligand | Conv. (%) | Selectivity Pentenal (%) | Pentanal (%) | Dialdehydes (%) |
|---|---|---|---|---|---|
| 21 | 2 | 91.0 | 75.5 | 1.7 | 8.4 |
| 22 | 1 | 94.4 | 70.0 | 3.1 | 12.6 |
| 23 | 4 | 95.8 | 75.9 | 4.6 | 7.5 |
| 24 | 2* | 94.5 | 95.1 | 3.1 | 0.0 |

*6/1 ligand/Rh; other examples were run at 3/1 Ligand/Rh

These results show that 3-pentenal can be obtained in high yield and rate with the catalysts of this invention.

14

We claim:

1. Process for the preparation of a linear aldehyde organic compound starting from an ethylenically unsaturated organic compound by hydroformylation in the presence of a catalyst system comprising a Group VIII metal and a bidentate organic ligand having two trivalent phosphorus atoms, characterized in that the two phosphorus atoms are linked with a 2,2'-dihydroxyl-1,1'-binapthalene or 2,2'-dihydroxyl-1,1'-biphenylene bridging group (Q). The ligand has the structure:

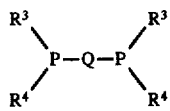

R$^3$ and R$^4$ are the same or different aryl or nitrogen containing heterocycle groups, where the nitrogen is bound to the phosphorus.

2. Process according to claim 1, characterized in that Q is substituted in the 3,3' position with R$^1$ and R$^2$, where R$^1$ and R$^2$ are selected from the group of H, alkyl, aryl, triarylsilyl, trialkylsilyl, carboalkoxy, carboaryloxy, aryloxy, alkoxy, alkylcarbonyl, arylcarbonyl, amide, halogen, and a nitrile.

3. Process according to claim 2, characterized in that R$^1$ and R$^2$ are carboalkoxyl groups, CO$_2$R, in which R is C$_1$–C$_{20}$ alkyl or C$_6$–C$_{20}$ aryl.

4. Process according to claim 1, characterized in that R$^3$ and R$^4$ are monovalent aryl groups containing at least one R$^6$ group other than hydrogen in the meta- or para-position relative to the phosphorus atom.

5. Process according to claim 4, characterized in that R$^6$ is C$_1$–C$_{20}$ alkyl, C$_6$–C$_{20}$ aryl, F, Cl, Br, CF$_3$.

6. Process according to claim 5, characterized in that R$^6$ is CF$_3$, F, or Cl in a meta or para-position relative to the phosphorus atom and R$^1$ and R$^2$ are carboalkoxy groups according to —CO2R in which R is C$_1$–C$_8$ alkyl.

7. Process according to claim 1 where R$^3$ and R$^4$ are optionally substituted pyrrole or indole groups.

8. Process according to claim 1, characterized in that the Group VIII metal is rhodium.

9. Process according to claim 1, characterized in that the ethylenically unsaturated compound has 2 to 20 carbon atoms.

10. Process according to claim 9, characterized in that the ethylenically unsaturated organic compound is an internally ethylenically unsaturated compound with 4 to 20 carbon atoms.

11. Process according to claim 10, characterized in that the internally ethylenically unsaturated compound is 3-pentenenitrile, 3-pentenoic acid, or a C$_1$–C$_6$ alkyl 3-pentenoate ester compound.

12. Process according to claim 11, characterized in that the internally ethylenically unsaturated compound is methyl 3-pentenoate.

13. Process according to claim 1 wherein the solvent is selected from the group consisting of aromatic hydrocarbons, ketones, aldehydes, ethers, esters, sulfones and nitriles.

14. Process according to claim 13 in which the solvent is the starting olefinic substrate and its hydroformylation products.

15. Process according to claim 14 in which the solvent is the high boiling residue remaining after separation of the major products by distillation.

16. Process according to claim 1 wherein the metal is rhodium at a concentration of 10 to 5000 parts per million, the ligand to rhodium ratio is 0.5 to 20, the temperature is in the range 40° C. to 140° C., the total pressure is in the range 0.1 to 20 MPa, and the CO/H$_2$ ratio is 0.1 to 10.

17. Process according to claim 1, characterized in that the ethylenically unsaturated organic compound is butadiene, the Group VIII metal is rhodium, and $R^1$ and $R^2$ are carboalkoxy groups, —CO—OR, in which R is $C_1$–$C_8$ alkyl.

18. Process according to claim 17, characterized in that $R^3$ and $R^4$ are aryl groups substituted in at least one meta or para position with $R^6$, where $R^6$ is selected from the group of alkyl, aryl, CF$_3$, F, or Cl.

19. Process according to claim 17, characterized in that $R^3$ and $R^4$ are pyrrolyl or indolyl groups.

20. Process according to claim 1, characterized in that the ethylenically unsaturated organic compound is an internally ethylenically unsaturated compound with 4 to 20 carbon atoms, the Group VIII metal is rhodium, and $R^1$ and $R^2$ are carboalkoxy groups, —CO$_2$R, in which R is $C_1$–$C_8$ alkyl.

21. Process according to claim 20, characterized in that $R^3$ and $R^4$ are aryl groups substituted in at least one meta or para position with $R^6$, where $R^6$ is selected from the group of alkyl, aryl, CF$_3$, F, or Cl.

22. Process according to claim 20, characterized in that $R^3$ and $R^4$ are pyrrolyl or indolyl groups.

23. A hydroformylation catalyst composition comprising rhodium and a bidentate organic ligand having two trivalent phosphorus atoms,

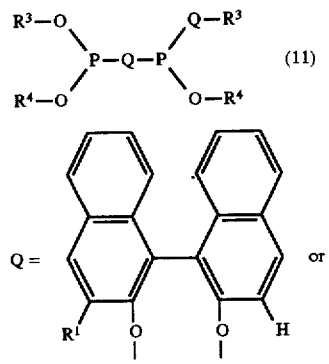

(11)

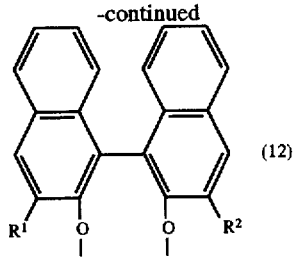

(12)

in which the two phosphorus atoms are linked with a 2,2'-dihydroxyl-1,1'-binapthalene bridging group (Q), which bridging group has substituents $R^1$ and $R^2$ in the 3,3'-positions, where $R^1$ and $R^2$ can be hydrogen or a substituent other than hydrogen, in which $R^3$ and $R^4$ are the same or different monovalent aryl groups or where $R^3$ and $R^4$ are the same or different nitrogen containing heterocycle groups, where the nitrogen is bound to phosphorus.

24. Composition according to claim 23, characterized in that Q is substituted in the 3,3' position with $R^1$ and $R^2$, where $R^1$ and $R^2$ are selected from the group of H, alkyl, aryl, triarylsilyl, trialkylsilyl, carboalkoxy, carboaryloxy, aryloxy, alkoxy, alkylcarbonyl, arylcarbonyl, amide, halogen, and a nitrile.

25. Composition according to claim 24, characterized in that $R^1$ and $R^2$ are carboalkoxyl groups, CO$_2$R, in which R is $C_1$–$C_{20}$ alkyl or $C_6$–$C_{20}$ aryl.

26. Composition according to claim 23, characterized in that $R^3$ and $R^4$ are monovalent aryl groups containing at least one $R^6$ group other than hydrogen in the meta- or para-position relative to the phosphorus atom.

27. Composition according to claim 26, characterized in that $R^6$ is $C_1$–$C_{20}$ alkyl, $C_6$–$C_{20}$ aryl, F, Cl, Br, CF$_3$.

28. Composition according to claim 27, characterized in that $R^6$ is CF$_3$, F, or Cl in a meta or para-position relative to the phosphorus atom and $R^1$ and $R^2$ are carboalkoxy groups according to —CO$_2$R in which R is $C_1$–$C_8$ alkyl.

29. Composition according to claim 23 where $R^3$ and $R^4$ are optionally substituted pyrrole or indole groups.

* * * * *

UNITED STATES PATENT AND TRADEMARK OFFICE
CERTIFICATE OF CORRECTION

PATENT NO. : 5,710,344
DATED : January 20, 1998
INVENTOR(S) : Anne Irsa Breikss, et. al.

It is certified that error appears in the above-identified patent and that said Letters Patent is hereby corrected as shown below:

Col. 15 and 16, delete Claim 23 (line 25 to line 20, and substitute--
  23. A hydroformylation catalyst composition comprising rhodium and a
bidentate organic ligand having two trivalent phosphorus atoms,

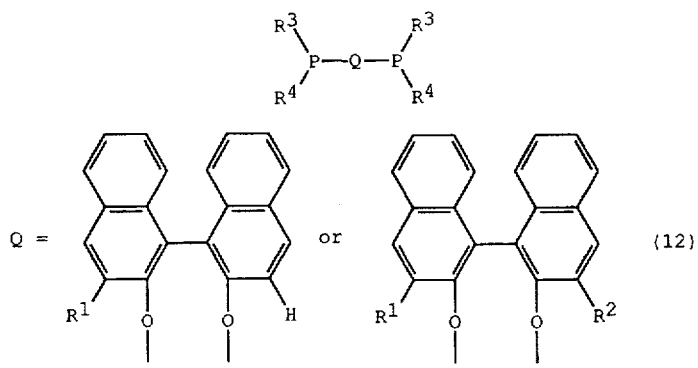

(12)

UNITED STATES PATENT AND TRADEMARK OFFICE
CERTIFICATE OF CORRECTION

PATENT NO. : 5,710,344
DATED : Janaury 20, 1998
INVENTOR(S) : Anne Irsa Breikss, et. al.

It is certified that error appears in the above-identified patent and that said Letters Patent is hereby corrected as shown below:

in which the two phosphorus atoms are linked with a 2,2'-dihydroxyl-1,1'-binapthalene bridging group (Q), which bridging group has substituents $R^1$ and $R^2$ in the 3,3'-positions, where $R^1$ and $R^2$ are a substituent other than hydrogen, in which $R^3$ and $R^4$ are the same or different monovalent aryl groups or where $R^3$ and $R^4$ are the same or different nitrogen containing heterocycle groups, where the nitrogen is bound to phosphorus. --

Signed and Sealed this

Sixth Day of April, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.    : 5,710,344
DATED         : January 20, 1998
INVENTOR(S)   : Breikss et al.

It is certified that error appears in the above-identified patent and that said Letters Patent is hereby corrected as shown below:

Column 3,
Line 44, replace "C(O)N(R5)" with -- C(O)N($R^5$) --
Line 45, replace "(R7) where R5, R7" with -- ($R^7$) where $R^5$, $R^7$ --
Line 45, replace "C1 to C10" with -- $C_1$ to $C_{10}$ --
Line 47, replace "C2 to C10" with -- $C_2$ to $C_{10}$ --

Column 9,
Line 8, replace "CO" with -- $CO/H_2$ --

Column 10,
Line 60, replace "ligand 2" with -- Lignad 2 --
Line 61, replace "ligand 3" with -- Ligand 3 --

Column 13,
Line 37, delete "247-2B."

Column 14,
Line 9, replace "(Q). The lignad has" with -- (Q); said ligand having --
Line 33, replace "Br, $CF_3$" with -- Br or $CF_3$ --
Line 37, replace "–CO2R" with -- –$CO_2R$ --

Column 15,
Line 7, replace "–CO-OR" with -- –$CO_2R$ --

Column 16,
Line 36, replace "Br, $CF_3$" with -- Br or $CF_3$ --

UNITED STATES PATENT AND TRADEMARK OFFICE
CERTIFICATE OF CORRECTION

PATENT NO.    : 5,710,344
DATED         : January 20, 1998
INVENTOR(S)   : Breikss et al.

It is certified that error appears in the above-identified patent and that said Letters Patent is hereby corrected as shown below:

Column 15, line 25 to Column 16, line 20,
Please delete Claim 23 and substitute

-- 23. A hydroformylation catalyst composition comprising rhodium and a bidentate organic ligand having two trivalent phosphorus atoms,

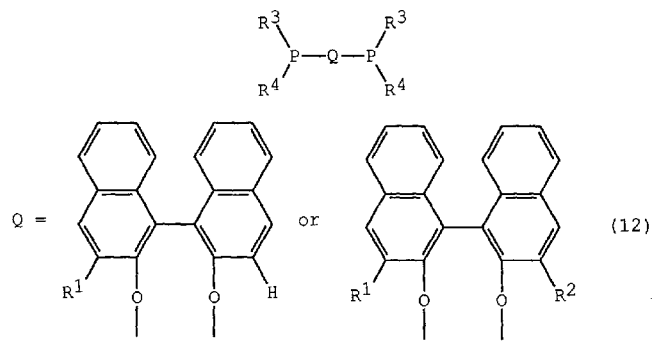

in which the two phosphorus atoms are linked with a 2,2'-dihydroxyl-1,1'-binapthalene bridging group (Q), which bridging group has substituents $R^1$ and $R^2$ in the 3,3'-positions, where $R^1$ and $R^2$ are a substituent other than hydrogen, in which $R^3$ and $R^4$ are the same or different monovalent aryl groups or where $R^3$ and $R^4$ are the same or different nitrogen containing heterocycle groups, where the nitrogen is bound to phosphorus. --

Signed and Sealed this

Thirteenth Day of May, 2003

JAMES E. ROGAN
*Director of the United States Patent and Trademark Office*